US009295495B2

(12) United States Patent
Tornier et al.

(10) Patent No.: US 9,295,495 B2
(45) Date of Patent: Mar. 29, 2016

(54) POSTERIOR LUMBAR JOINT PROSTHESIS

(75) Inventors: Alain Tornier, Saint-Ismier (FR);
Jean-Paul Steib, Strasbourg (FR);
Christian Mazel, Boulogne Billancourt (FR)

(73) Assignee: CLARIANCE, Dainville (FR)

( * ) Notice: Subject to any disclaimer, the term of this patent is extended or adjusted under 35 U.S.C. 154(b) by 1333 days.

(21) Appl. No.: 12/391,519

(22) Filed: Feb. 24, 2009

(65) Prior Publication Data

US 2009/0216277 A1    Aug. 27, 2009

Related U.S. Application Data

(60) Provisional application No. 61/033,040, filed on Mar. 3, 2008.

(30) Foreign Application Priority Data

Feb. 26, 2008 (FR) .................................... 08/01020

(51) Int. Cl.
*A61B 17/70* (2006.01)
*A61F 2/44* (2006.01)

(52) U.S. Cl.
CPC ......... *A61B 17/7041* (2013.01); *A61B 17/7011* (2013.01); *A61B 17/7023* (2013.01); *A61B 17/7025* (2013.01); *A61B 17/7064* (2013.01);
(Continued)

(58) Field of Classification Search
CPC ............. A61B 17/562; A61B 17/7001; A61B 17/7002; A61B 17/7004; A61B 17/7005; A61B 17/7007; A61B 17/7008; A61B 17/702; A61B 17/701; A61B 17/704; A61B 17/7011; A61B 17/7014; A61B 17/7025; A61B 17/7023; A61B 17/7032; A61B 17/7034; A61B 17/7035; A61B 17/7038; A61B 17/7041; A61B 17/7043; A61B 17/7046; A61B 17/7064; A61B 17/8047; A61B 17/8685; A61B 17/8695; A61B 17/7049; A61B 17/7062
USPC ........... 606/60, 246, 247, 254–260, 264, 265, 606/279
See application file for complete search history.

(56) References Cited

U.S. PATENT DOCUMENTS

| 5,501,684 | A | * | 3/1996 | Schlapfer | ............... A61B 17/60 403/90 |
| 5,522,816 | A | * | 6/1996 | Dinello | .............. A61B 17/7052 403/400 |
| 5,814,046 | A | * | 9/1998 | Hopf | .................. A61B 17/7082 606/264 |

(Continued)

*Primary Examiner* — Pedro Philogene
*Assistant Examiner* — Lynnsy Summitt
(74) *Attorney, Agent, or Firm* — Young & Thompson

(57) ABSTRACT

There is provided a posterior lumbar joint prosthesis which includes prosthetic elements reproducing the movements of the joint facets and vertebral anchors which adapt to the variations in the anatomy of vertebra. In use, the prosthesis has lower and upper connectors on each side of the lumbar vertebra. The lower connectors are coupled with, and pivotably mounted onto, respective lower pedicular screws, and a member defining a member axis links lower and upper connectors on each side of the lumbar vertebra. Upon lateral flexion of one of the upper and lower vertebrae relative to the other, each lower connector is capable of multiaxis pivotable movement relative to the respective lower pedicular screws such that each member is capable to pivot with respect to (i) the axis of the lower screw, (ii) a first axis intersecting the lower screw and the lower connector, and/or (iii) an axis intersecting the above first axis and the lower screw, while the member can also move along the member axis.

3 Claims, 8 Drawing Sheets

(52) U.S. Cl.
CPC ......... *A61B 17/7032* (2013.01); *A61B 17/7035* (2013.01); *A61F 2/4405* (2013.01)

(56) References Cited

U.S. PATENT DOCUMENTS

| | | | | |
|---|---|---|---|---|
| 6,187,005 B1* | 2/2001 | Brace | ................ | A61B 17/7035 606/264 |
| 6,231,575 B1* | 5/2001 | Krag | ................ | A61B 17/7041 606/264 |
| 7,083,622 B2* | 8/2006 | Simonson | ......... | A61B 17/7007 606/253 |
| 7,104,993 B2* | 9/2006 | Baynham | ........... | A61B 17/7052 606/252 |
| 2003/0060823 A1* | 3/2003 | Bryan | ................ | A61B 17/7011 606/86 A |
| 2004/0116928 A1* | 6/2004 | Young | ................ | A61B 17/7052 606/253 |
| 2005/0010214 A1* | 1/2005 | Tassin | ................ | A61B 17/7007 606/261 |
| 2005/0070901 A1* | 3/2005 | David | ................ | A61B 17/7041 606/278 |
| 2005/0177164 A1* | 8/2005 | Walters | .............. | A61B 17/7007 606/86 A |
| 2006/0015100 A1* | 1/2006 | Panjabi | .............. | A61B 17/7007 74/1 R |
| 2006/0189984 A1* | 8/2006 | Fallin | ................. | A61B 17/7007 606/250 |
| 2006/0217710 A1* | 9/2006 | Abdou | ............... | A61B 17/6433 606/54 |
| 2006/0217719 A1* | 9/2006 | Albert | ................ | A61B 17/7011 606/261 |
| 2006/0271046 A1* | 11/2006 | Kwak | ................ | A61B 17/7023 606/250 |
| 2007/0167946 A1* | 7/2007 | Triplett | .............. | A61B 17/1757 606/279 |
| 2007/0270843 A1* | 11/2007 | Matthis | .............. | A61B 17/701 606/86 A |
| 2008/0140134 A1* | 6/2008 | Markworth | ........ | A61B 17/7011 606/308 |
| 2008/0319489 A1* | 12/2008 | Triplett | .............. | A61B 17/7067 606/301 |

* cited by examiner

POSTERIOR LUMBAR JOINT PROSTHESIS

CROSS-REFERENCE TO RELATED APPLICATIONS

This application claims the benefit of U.S. Provisional Patent Application 61/033,040, filed on Mar. 3, 2008 and of French Patent Application 08/01020, filed on Feb. 26, 2008, the contents of which are incorporated herein by reference in their entirety.

FIELD OF THE INVENTION

The present invention relates to a posterior lumbar joint prosthesis allowing flexing and extension movements, lateral flexion, and rotation concomitant with lateral flexion of the upper and lower lumbar vertebrae.

BACKGROUND OF THE INVENTION

Degeneration of the vertebral joints may lead to arthrosis (osteoarthritis) of the facets that may manifest itself as a reduction in cartilage thickness, which may lead to the complete disappearance of the cartilage and thus generate friction on degenerated joint facets. Osteophytes which are protrusions of bone and cartilage are very common and develop in areas of a degenerating joint as a reparative response by the remaining cartilage. Such protrusions are largely responsible for limitations in joint motion and can also cause pain. These phenomena have been identified as being responsible for lumbagos and radiculalgia that affect a significant portion of the population.

Hence, there is a need to reduce and/or remove friction on damaged, injured, diseased, or otherwise degenerated joint facets and/or to minimize transfer of the forces normally absorbed by the intervertebral spaces onto the joint facets of neighboring and subjacent vertebra, while retaining mobility of the vertebral joints.

PCT Application WO 06/073593 relates to a device for replacing damaged, injured, diseased, or otherwise unhealthy posterior elements, such as the facet joints of a patient's spinal column. This device includes two stabilizing implants, each implant having two lengthwise members which connect an upper and lower vertebrae, via a respective upper and lower pedicular screws. The two lengthwise members are coupled to each other via coupling means. Movement between the upper and lower vertebrae is permitted by the coupling means used between the two lengthwise members. However, this device does not permit mobility of each member relative to the respective pedicular anchors thus limiting mobility to some extent.

U.S. Pat. No. 7,029,475 relates to a dynamic spine stabilizer device, which includes a support assembly and a resistance assembly associated with the support assembly. Ball joints link this device with pedicular screws that are anchored to upper and lower vertebrae. The junction of the dynamic spine stabilizer and pedicular screws is free and rotationally unconstrained. However, the goal of such a device is not to replace degenerated anatomical structures while facilitating motion, but rather to stabilize and control abnormal spinal motion. Indeed, in use, when the upper and lower vertebrae are moved in flexion, this device is adapted to create resistance to the movement of the spine. Through such mechanism, as the spine moves in flexion from the initial position, the device increases resistance thus stabilizing the movement.

Known devices present certain disadvantages regarding, for instance but not limited to, obstruction, kinematics, mobility, friction, positioning and/or the quality of the anchors. It is difficult, for instance, to ensure that the anchors be of a uniform quality in terms of positioning and strength due to variations in form from one vertebra to another and/or between one patient and another. These difficulties may not only lead to bad kinematics of movement but also to degradation of the functional unit (two adjacent vertebrae).

Therefore, there is a need for a prosthesis that preserves intervertebral mobility, while removing friction from between the joint facets, and which prosthesis includes anchors that adapt to the variations in the anatomy of vertebrae and variations due to the surgical technique itself.

SUMMARY OF THE INVENTION

In a broad aspect, there is provided a posterior lumbar joint prosthesis which includes prosthetic elements reproducing the movements of the joint facets and vertebral anchors which adapt to the variations in the anatomy of vertebrae. In one embodiment, such prosthesis provides for a simple and intuitive installation by the surgeon.

The invention provides a posterior lumbar joint prosthesis for an upper and a lower lumbar vertebrae, the upper lumbar vertebra having left and right upper pedicles and the lower lumbar vertebra having left and right lower pedicles, the prosthesis comprising: (a) a left upper pedicular screw extending along a left upper axis, the left upper pedicular screw having a lower threaded portion being anchored in the left upper pedicle; (b) a right upper pedicular screw extending along a right upper axis, the right upper pedicular screw having a lower threaded portion being anchored in the right upper pedicle; (c) a left lower pedicular screw extending along a left lower axis, the left lower pedicular screw having upper and lower threaded portions, the lower threaded portion being anchored in the left lower pedicle; (d) a right lower pedicular screw extending along a right lower axis, the right lower pedicular screw having upper and lower threaded portions, the lower threaded portion being anchored in the right lower pedicle; (e) left and a right lower connectors, each respectively coupled to the left and right lower pedicular screws; (f) a left member for linking the left upper pedicular screw and the lower connector, the left member extending along a left member axis and having a lower end and an upper lateral projection linked to the left upper pedicular screw, the left member axis being spaced from the left lower axis; (g) a right member for linking the right upper pedicular screw and the lower connector, the right member extending along a right member axis and having a lower end and an upper lateral projection linked to the right upper pedicular screw, the right member axis being spaced from the right lower axis; wherein each lower pedicular screw extends through the second aperture of each lower connector and wherein each member extends through the first aperture of each lower connector; and wherein, in use, lateral flexion of one of the upper and lower vertebrae relative to the other imparts either or both (i) movement of one member along the member axis with respect to the first aperture of the lower connector and (ii) pivotable movement of the member relative to the lower axis.

The invention also provides a posterior lumbar joint prosthesis for an upper and a lower lumbar vertebrae, the upper lumbar vertebra having left and right upper pedicles and the lower lumbar vertebra having left and right lower pedicles, the prosthesis comprising: (a) a left upper pedicular screw extending along a left upper axis, the left upper pedicular screw having a lower threaded portion being anchored in the left upper pedicle; (b) a right upper pedicular screw extending along a right upper axis, the right upper pedicular screw having a lower threaded portion being anchored in the right upper pedicle; (c) a left lower pedicular screw extending along a left lower axis, the left lower pedicular screw having upper and lower threaded portions, the lower threaded portion being anchored in the left lower pedicle; (d) a right lower pedicular screw extending along a right lower axis, the right lower pedicular screw having upper and lower threaded portions, the lower threaded portion being anchored in the right lower pedicle; (e) left and a right lower connectors, each respectively coupled to the left and right lower pedicular screws; (f) a left member for linking the left upper pedicular screw and the lower connector, the left member extending along a left member axis and having a lower end and an upper lateral projection linked to the left upper pedicular screw, the left member axis being spaced from the left lower axis; (g) a right member for linking the right upper pedicular screw and the lower connector, the right member extending along a right member axis and having a lower end and an upper lateral projection linked to the right upper pedicular screw, the right member axis being spaced from the right lower axis; wherein each of the left and right lower connectors has a body having an internal peripheral wall defining a first aperture encircling each member axis and a connecting portion having a second aperture encircling each lower axis, wherein each lower pedicular screw extends through the second aperture of each lower connector and wherein each member extends through the first aperture of each lower connector; and wherein the prosthesis comprises left and right sleeves, each of the left and right sleeves having a spherical portion with an external convex peripheral surface and being mounted on the upper threaded portion of each lower pedicular screw and within the second aperture of the connecting portion of each lower connector and wherein the connecting portion of each lower connector has an internal concave peripheral wall following the external convex peripheral surface of the sleeve such that each lower connector is pivotably mounted with respect to the sleeve and such that, in use, lateral flexion of one of the upper and lower vertebrae relative to the other imparts either or both (i) movement of one member along the member axis with respect to the first aperture of the lower connector and (ii) pivotable movement of the member relative to the lower axis, and further imparts pivotable movement of the member relative to either or both (iii) a first lower pivoting axis intersecting the member axis and the lower axis and (iv) a second lower pivoting axis, parallel to the member axis, and intersecting the lower axis and the first lower pivoting axis.

The invention further provides a posterior lumbar joint prosthesis for an upper and a lower lumbar vertebrae, the upper lumbar vertebra having left and right upper pedicles and the lower lumbar vertebra having left and right lower pedicles, the prosthesis comprising: (a) a left upper pedicular screw extending along a left upper axis, the left upper pedicular screw having a lower threaded portion being anchored in the left upper pedicle; (b) a right upper pedicular screw extending along a right upper axis, the right upper pedicular screw having a lower threaded portion being anchored in the right upper pedicle; (c) a left lower pedicular screw extending along a left lower axis, the left lower pedicular screw having upper and lower threaded portions, the lower threaded portion being anchored in the left lower pedicle; (d) a right lower pedicular screw extending along a right lower axis, the right lower pedicular screw having upper and lower threaded portions, the lower threaded portion being anchored in the right lower pedicle; (e) left and a right lower connectors, each respectively coupled to the left and right lower pedicular screws; (f) a left member for linking the left upper pedicular screw and the lower connector, the left member extending along a left member axis and having a lower end and an upper lateral projection linked to the left upper pedicular screw, the left member axis being spaced from the left lower axis; (g) a right member for linking the right upper pedicular screw and the lower connector, the right member extending along a right member axis and having a lower end and an upper lateral projection linked to the right upper pedicular screw, the right member axis being spaced from the right lower axis; wherein each of the left and right lower connectors has a body having an internal peripheral wall defining a first aperture encircling each member axis and a connecting portion having a second aperture encircling each lower axis, wherein each lower pedicular screw extends through the second aperture of each lower connector and wherein each member extends through the first aperture of each lower connector; wherein the prosthesis comprises left and right sleeves, each of the left and right sleeves having a spherical portion with an external convex peripheral surface and being mounted on the upper threaded portion of each lower pedicular screw and within the second aperture of the connecting portion of each lower connector and wherein the connecting portion of each lower connector has an internal concave peripheral wall following the external convex peripheral surface of the sleeve such that each lower connector is pivotably mounted with respect to the sleeve and such that, in use, lateral flexion of one of the upper and lower vertebrae relative to the other imparts either or both (i) movement of one member along the member axis with respect to the first aperture of the lower connector and (ii) pivotable movement of the member relative to the lower axis, and further imparts pivotable movement of the member relative to either or both (iii) a first lower pivoting axis intersecting the member axis and the lower axis and (iv) a second lower pivoting axis, parallel to the member axis, and intersecting the lower axis and the first lower pivoting axis; and wherein the prosthesis comprises left and right lower nuts, wherein each sleeve has an upper portion extending above the connecting portion of the lower connector and wherein each lower nut is tightened on the upper threaded portion of each lower pedicular screw such that it abuts and maintains in place each sleeve while allowing pivotable movements of the lower connector with respect to the sleeve.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

A detailed description of the embodiments of the present invention is provided herein below, by way of example only, with reference to the accompanying drawings, in which.

Figure 1:
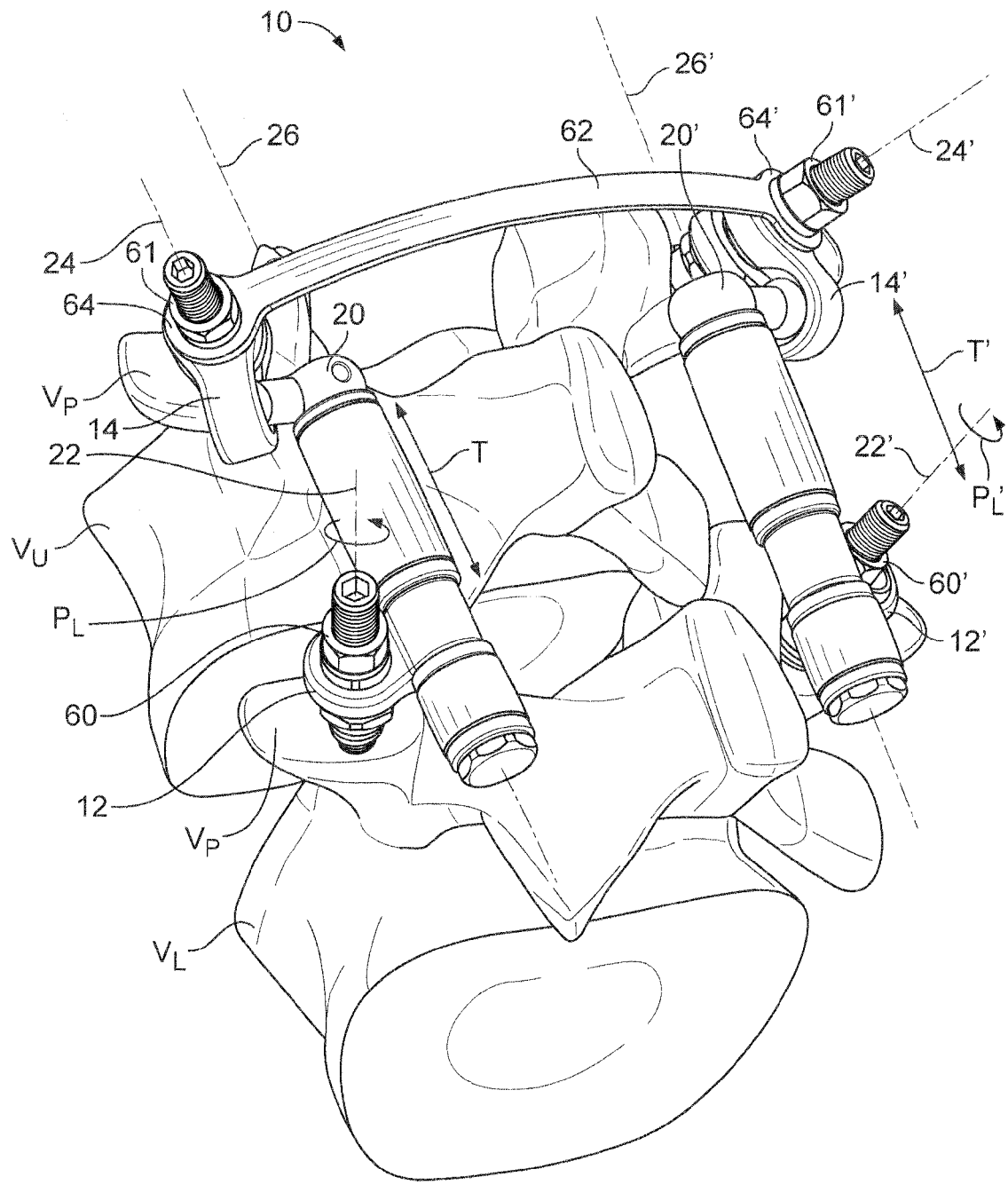
FIG. 1 is a perspective view of a posterior lumbar joint prosthesis in accordance with an embodiment of the present invention.

In the drawings, embodiments of the invention are illustrated by way of examples. It is to be expressly understood that the description and drawings are only for the purpose of illustration and are an aid for understanding. They are not intended to be a definition of the limits of the invention.

DETAILED DESCRIPTION OF EMBODIMENTS OF THE INVENTION

To facilitate the description, any reference numeral designating an element in one figure will designate the same element if used in any other figures. In describing the embodiments, specific terminology is resorted to for the sake of clarity but the invention is not intended to be limited to the specific terms so selected, and it is understood that each specific term comprises all equivalents.

Unless otherwise indicated, the drawings are intended to be read together with the specification, and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate.

In FIG. 1, an instrumented spinal segment of a vertebral column is shown of which an upper and lower lumbar vertebrae $V_U$, $V_L$ are connected to each other on each side of the lumbar column by a posterior lumbar joint prosthesis 10 constructed in accordance with an embodiment of the present invention.

Referring to FIGS. 1 to 6, the prosthesis 10 has left and right lower connectors 12, 12', which are coupled to respective left and right lower pedicular screws 16, 16', and left and right upper connectors 14, 14' that are coupled to respective left and right upper pedicular screws 18, 18'. The screws 16, 16' are anchored in the left and right pediculi $V_P$ of the lower lumbar vertebra $V_L$ and the screws 18, 18' are anchored in the left and right pediculi $V_P$ of the upper vertebra $V_U$.

Figure 2:
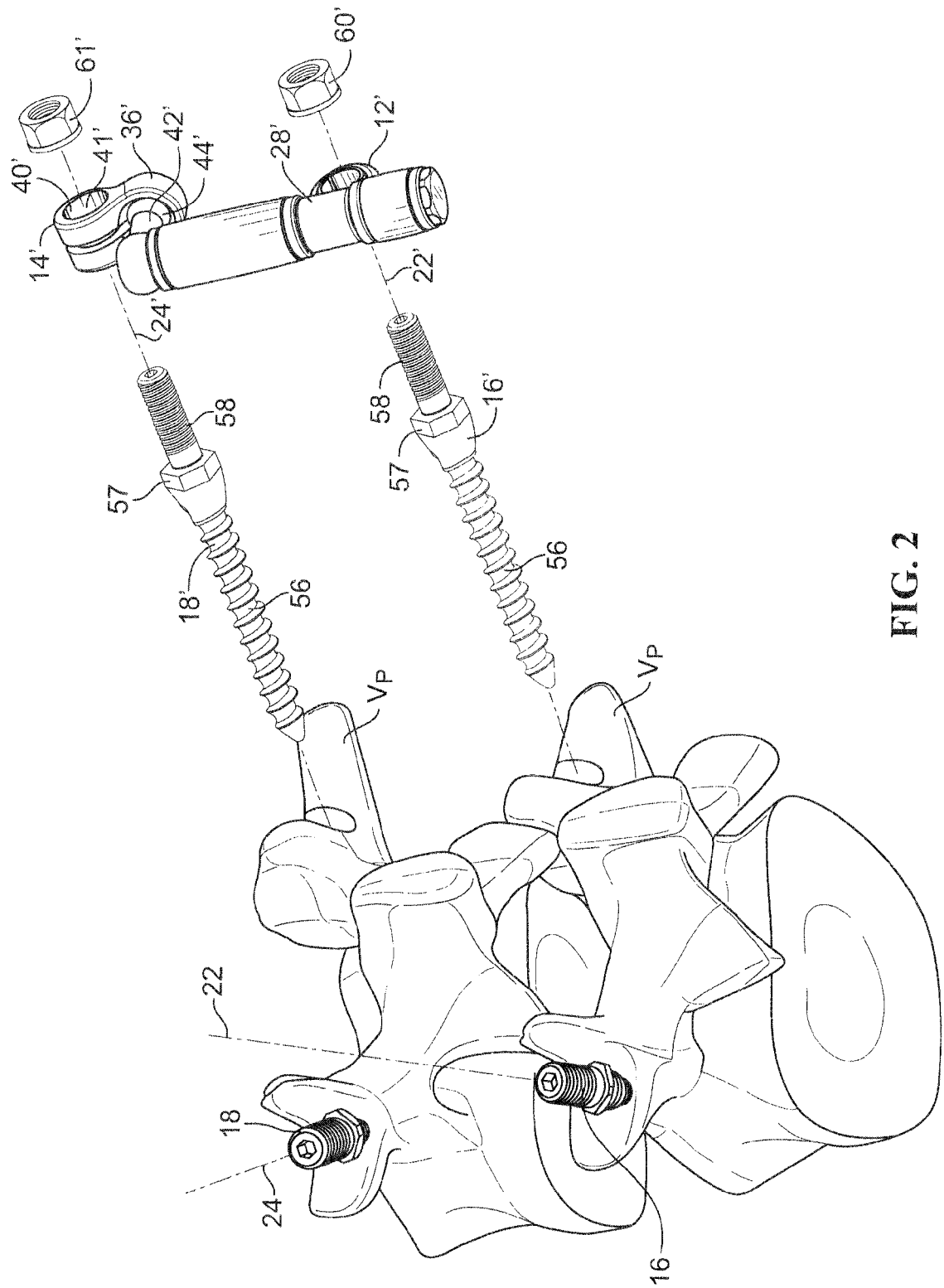
FIG. 2 is a perspective view showing two pedicular screws anchored in the left upper and lower lumbar vertebrae ($V_U$, $V_L$) of the instrumented spinal segment, two pedicular screws to be anchored in the right upper and lower lumbar vertebrae ($V_U$, $V_L$) and right upper and lower connectors with a right member linking them, of the prosthesis shown in FIG. 1.
Figure 6:
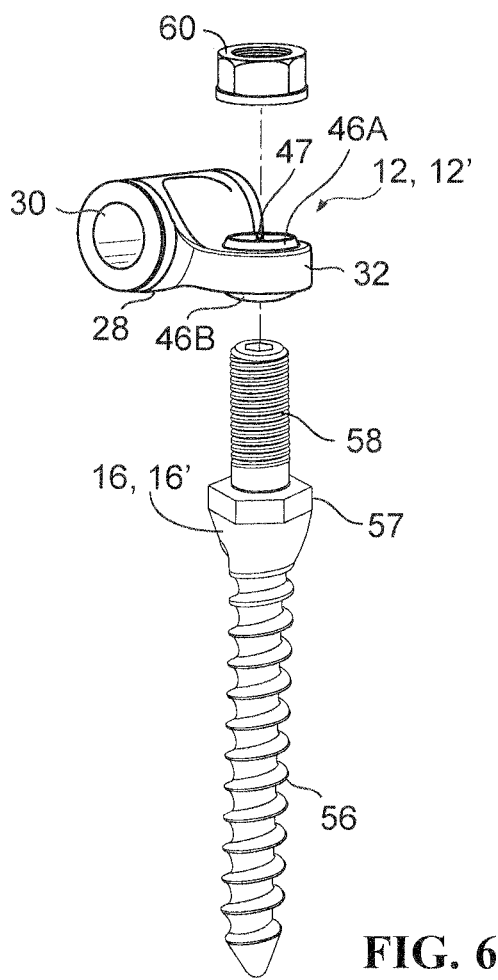
FIG. 6 is an enlarged exploded perspective view of one pedicular screw, lower connector, sleeve and nut.

Referring to FIGS. 2 and 6, the lower 16 (or 16') and upper (18, 18') pedicular screws each have an upper threaded portion 58, a shoulder 57 and a lower threaded portion 56 that is adapted to be anchored in the pedicle $V_P$. In one embodiment, the pedicular screws 16, 16' and/or 18, 18' may be cannulated with side openings. Such openings may allow the injection, for instance, of biological cement intended to improve anchoring within each lower and upper lumbar vertebrae $V_L$, $V_U$ of the spinal segment to be instrumented.

The person skilled in the art will appreciate that the lower threaded portion 56 of each pedicular screw is intended for anchoring the pedicular screw within the bony body of the pedicles $V_P$ of each respective lower and upper lumbar vertebrae $V_L$, $V_U$ of the spinal segment to be instrumented according to methods known in the art.

As best shown in FIG. 1, the left and right lower pedicular screws 16, 16' define respective left and right lower axes 22, 22'. Similarly, the left and right upper pedicular screws 18, 18' define respective left and right upper axes 24, 24'. The prosthesis 10 comprises a left member 20 for linking the left lower and upper connectors 12, 14 on the left side of the lumbar vertebrae $V_L$, $V_U$ and a right member 20' for linking the right lower and upper connectors 12', 14' on the right side of the lumbar vertebrae $V_L$, $V_U$. The left and right members 20, 20' extend along respective left and right member axes 26, 26'.

Figure 3:
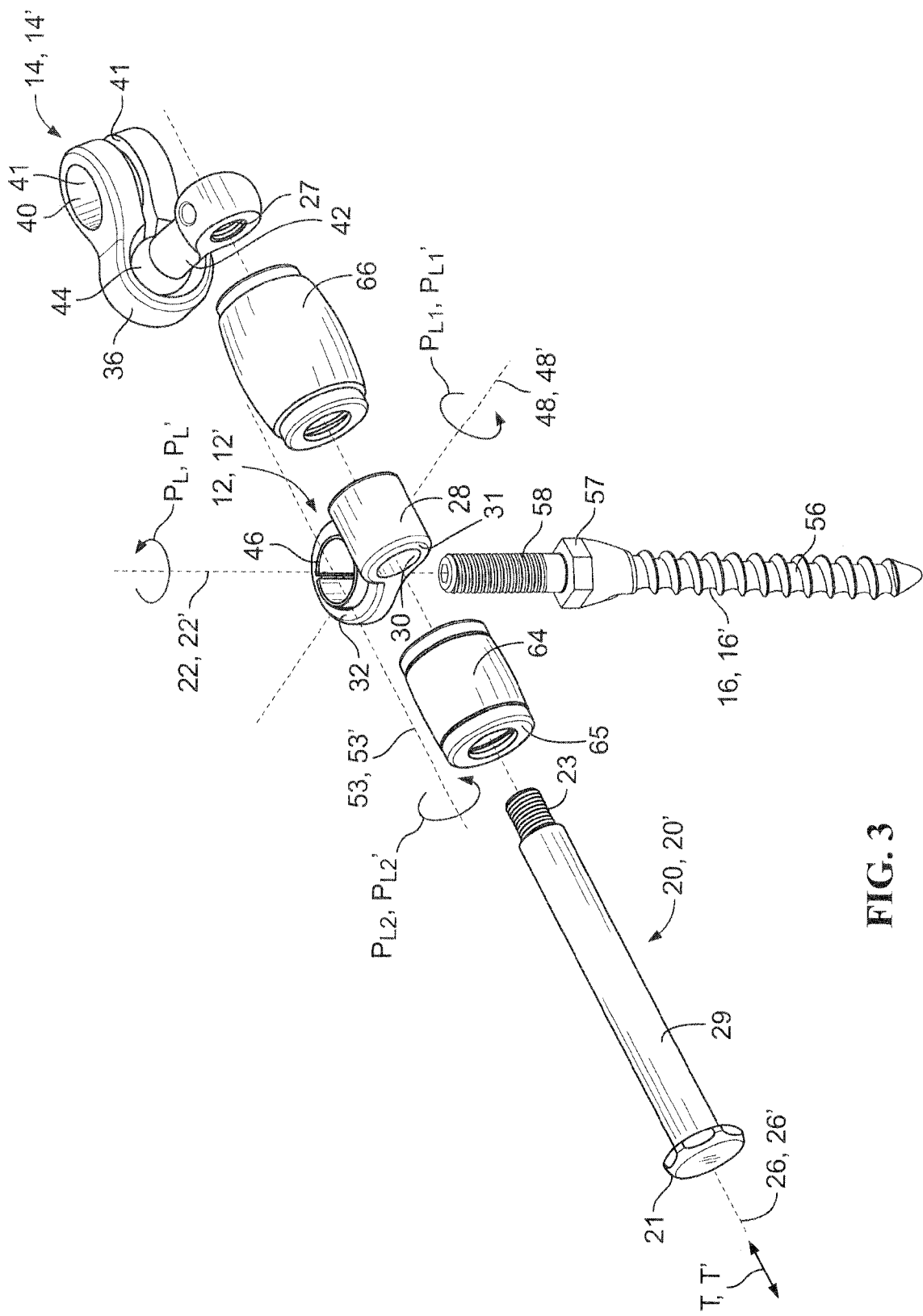
FIG. 3 is an enlarged exploded perspective view of the left upper and lower connectors and the left member shown in FIG. 1.
Figure 4:
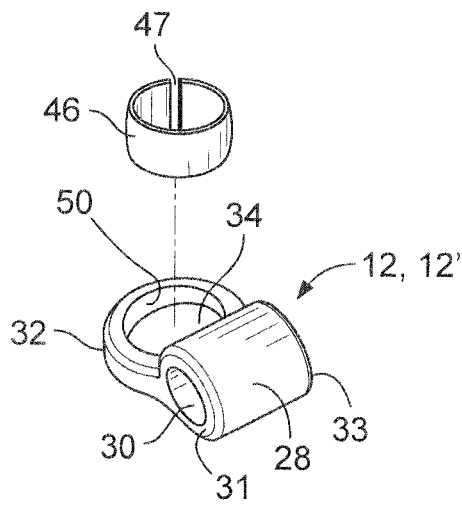
FIG. 4 is an enlarged perspective view of one lower connector and a sleeve.

As best shown in FIGS. 3 and 4, each of the left and right lower connectors 12, 12' has a body 28 having an internal peripheral wall defining a first aperture 30 encircling the member axis 26 (or 26') and a connecting portion 32 having a second aperture 34 encircling the lower axis 22 (or 22'). As shown in FIG. 3, the lower axis 22 (or 22') is a "vertical" axis while the member axis 26 (or 26') is a "horizontal" axis, the lower axis 22 (or 22') being spaced from the member axis 26 (or 26'). The member 20 (or 20') extends through the first aperture 30 of the lower connector 12 (or 12') and the lower pedicular screw 16 (or 16') extends through the second aperture 34.

Figure 5:
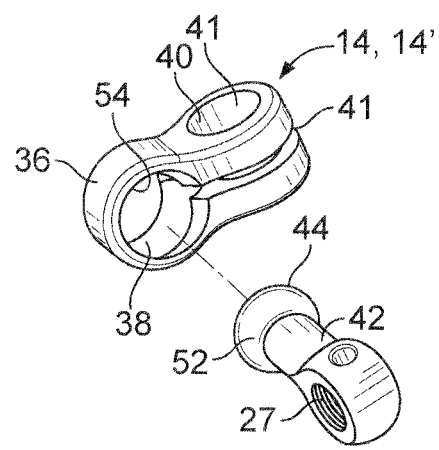
FIG. 5 is an enlarged perspective view of one upper connector and a component of the member.

Referring to FIG. 3, each of the left and right members 20, 20' has an upper lateral projection 42 with a threaded internal wall 27 and a rod 29 extending along the member axis, the rod 29 having a stop 21 at one extremity and a threaded section 23 at the opposite extremity. Through these components, the threaded section 23 and threaded internal wall 27 allows assembly of the rod 29 with the projection 42. It is understood that the member 20 (or 20') is formed of the rod 29 and the upper lateral projection 42. In that sense, the upper lateral projection 42 can be integrally formed with the rod 29 or, alternatively, can be detachably affixed to the rod 29. As best shown in FIG. 5, the upper lateral projection 42 of the member has a distal end 44 defining a ball 52.

As best shown in FIG. 4, the body 28 of the lower connector 12 (or 12') has a lower wall 31 and an upper wall 33. In one embodiment, the stop 21 of the member 20 (or 20') abuts against the lower wall 31 of the body 28 of the lower connector 12 (or 12') such that, in use, movement T (or T') of the member 20 (or 20') along the member axis 26 towards the upper vertebra $V_U$ is prevented when the stop 21 abuts the lower wall 31. In another embodiment, as shown in FIGS. 1 to 3, the prosthesis 10 may further include a lower absorbing element 64 and/or an upper absorbing element 66. When the optional element 64 is present, in use, movement T (or T') of the member 20 (or 20') along the member axis 26 towards the upper vertebra $V_U$ is prevented when the stop 21 abuts a lower wall 65 of the lower absorbing element 64. The elements 64 and/or 66 are made of a suitable material that may reduce shock impacts transmitted to the lower pedicular screw 16 (or 16'). One such suitable material may be, for instance but not limited to, polyurethane.

As best shown in FIGS. 2, 3 and 5, each of the left and right upper connector 14, 14' has a connecting portion 36 having a first aperture 38 for receiving the distal end 44 of the upper lateral projection 42 of the member 20 (or 20') and has a body with an internal peripheral wall 40 defining a second aperture 41 encircling the upper axis 24 (or 24') for receiving the upper pedicular screw 18 (or 18'), the first aperture 38 being spaced from the second aperture 40. The connecting portion 36 has an internal peripheral wall surrounding the first aperture 38 and defining a socket 54 in which the ball 52 of the upper lateral projection 42 can be mounted.

As best shown in FIGS. 3, 4 and 6 the connecting portion 32 of the lower connector 12 (or 12') has an internal concave peripheral surface 50 and the prosthesis 10 has a sleeve 46 that is at least partially received within the second aperture 34 of the connecting portion 32, the sleeve 46 having an external convex surface that is complementary to the internal concave peripheral surface 50 while there is a minimum clearance between these surfaces such that the lower connector 12 (or 12') can pivot relative to the sleeve 46. As shown in FIG. 4, the sleeve 46 may take the form of a ring having an external convex surface.

In one embodiment, the sleeve 46 has a split 47 in order to allow insertion of the sleeve 46 inside the second aperture 34 of the connecting portion 32 of the lower connector 12 (or 12') before installing the lower connector 12 (or 12') on the lower pedicular screw 16 (or 16').

As shown in FIGS. 1, 2 and 6, a tightening nut 60 (or 60') is used to affix the lower connector 12 (or 12') on the lower pedicular screw 16 (or 16'). The tightening nut 60 is fastened on the threaded portion 58 of each lower pedicular screw, according to general techniques that are well known in the art, and rests on top of the sleeve 46 in order to prevent any pivotable movement of the sleeve 46 and maintaining in place the sleeve 46 on the lower pedicular screw.

As best shown in FIG. 6, the sleeve 46 has a upper portion 46A and a bottom portion 46B, the respective top and bottom portions 46A, 46B extending slightly above and below the connecting portion 32 of the lower connector 12 (or 12'). The height of the sleeve 46 is therefore slightly larger than the one of the connecting portion 32 such that the bottom portion 46B abuts an upper surface of the shoulder 57 of the lower pedicular screw 16 (or 16') and the lower nut 60 (or 60') abuts against the upper portion 46A. Once the sleeve 46 is installed within second aperture 34 of the lower connector 12 (or 12'), the bottom portion 46B thus abuts the shoulder 57 and the upper portion 46A is above the connecting portion 32 thereby allowing each lower nut 60 (or 60') to abut each sleeve 46, and once tightened, maintaining in place each sleeve 46 on each lower pedicular screw 16 (or 16'). Because the nut 60 (or 60') does not contact the connection portion 32 of the lower connector 12 (or 12'), pivotable movements of the lower connector 12 (or 12') with respect to the sleeve 46 is therefore permitted.

Because the sleeve 46 is mounted and retained in place on the lower pedicular screw 16 (or 16'), and because the lower connector 12 (or 12') is pivotably mounted the lower connector 12 (or 12') (on the sleeve 46), during use, lateral flexion of one of the upper and lower vertebrae relative to the other imparts pivotable movement $P_L$ (or $P_L'$) of the member 20 (or 20') relative to the lower axis 22 (or 22') and/or translational movement T (or T') of the member 20 (or 20') along the member axis 26 (or 26'). The range of pivotable movement of the member 20 (or 20') relative of the lower axis 22 (or 22') can vary from −14° to 14°.

While the prosthesis 10 may have sleeves having a spherical portion with an external surface, or ball rings, it is understood that, instead of these sleeves or rings, each lower pedicular screw may comprise an integral spherical portion and the connecting portion 32 may have a split or other means such that it can be mounted on this spherical portion of the lower pedicular screw for allowing either or both pivotable movement $P_L$ (or $P_L'$) of the member 20 (or 20') relative to the lower axis 22 (or 22') and translational movement T (or T') of the member 20 (or 20') along the member axis 26 (or 26').

Referring to FIG. 3, because the sleeve 46 is mounted and retained in place on the lower pedicular screw 16 (or 16'), and because the lower connector 12 (or 12') is pivotably mounted on the sleeve 46, pivotable movement $P_{L1}$ (or $P_{L1}'$) of the member 20 (or 20') relative to a first lower pivoting axis 48 (or 48') intersecting the member axis 26 (or 26') and the lower axis 22 (or 22') is also permitted.

It is understood that when the member 20 (or 20') incurs a pivotable movement $P_{L1}$ (or $P_{L1}'$) relative to the first lower pivoting axis 48 (or 48'), so does the lower connector 12 (or 12') with respect to the sleeve 46. Indeed, pivotable movement $P_{L1}$ (or $P_{L1}'$) of the member 20 (or 20') relative to the lower pivoting axis 48 (or 48') imparts similar movement $P_{L1}$ (or $P_{L1}'$) of the body 28 that, in turn, imparts similar movement to the connecting portion 32, and thus to the whole lower connector 12 (or 12') with respect to the sleeve 46, which remains in place on the lower pedicular screw 16 (or 16').

With continuing reference to FIG. 3, there is also a second lower pivoting axis 53 (or 53'), parallel to the member axis 26 (or 26') and that intersects the first lower pivoting axis 48 (or 48') and the lower axis 22 (or 22'). Because the lower connector 12 (or 12') is pivotably mounted on the sleeve 46, pivotable movement $P_{L2}$ (or $P_{L2}'$) of the member 20 (or 20') relative to the second lower pivoting axis 53 (or 53') is also permitted. Again, it is understood that when the member 20 (or 20') incurs a pivotable movement $P_{L2}$ (or $P_{L2}'$) relative to the second lower pivoting axis 53 (or 53'), so does the lower connector 12 (or 12') with respect to the sleeve 46, which remains in place on the lower pedicular screw 16 (or 16').

As shown by FIG. 3, the first lower pivoting axis 48 (or 48') is a "horizontal" axis intersecting the lower axis 22 (or 22') at an angle of 90°. Similarly, the second lower pivoting axis 53 (or 53') is a "horizontal" axis intersecting the lower axis 22 (or 22') at an angle of 90°.

Upon lateral flexion of one of the upper and lower vertebrae relative to the other, each lower connector 12 (or 12') is therefore capable of pivotable movements relative to the sleeve 46 such that each member can pivot relative to the first lower pivoting axis (pivotable movement $P_{L1}$) and the second pivoting axes (pivotable movement $P_{L2}$). The range of pivotable movement of the member 20 (or 20') relative of the first lower pivoting axis 48 (or 48') can vary from −14° to 14° and the range of pivotable movement of the member 20 (or 20') relative of the second lower pivoting axis 53 (or 53') can vary from −14° to 14°.

Again, it is understood that pivotable movements $P_L$ (or $P_L'$), $P_{L1}$ (or $P_{L1}'$) and/or $P_{L2}$ (or $P_{L2}'$) of the member 20 (or 20') imparts corresponding pivotable movements of the lower connector 12 (or 12') with respect to the sleeve 46.

The prosthesis 10 allows flexing and extension movements, lateral flexion, and rotation concomitant with side flexing of the upper and lower lumbar vertebrae $V_U$, $V_L$ of the instrumented spinal segment.

As shown in FIGS. 1 and 2, in one embodiment, an upper nut 61 (or 61') screwed on the threaded portion of each upper pedicular screw is used to affix the upper connector 14 (or 14') on the upper pedicular screw 18 (or 18'). Moreover, as shown in FIG. 5, the body of the upper connector 14 (or 14') has a split 41 that allows deformation of the upper connector 14 (or 14') during tightening of the upper nut 61 (or 61'). Using techniques that are well known in the art, each upper nut 61 (or 61') is tightened such that the upper nut 61 (or 61') applies pressure on each upper connector 14 (or 14') and such that the ball 52 is maintained in place in the socket 55 for preventing any movement of the ball 52 with respect to the upper connector.

As shown in FIG. 1, the prosthesis 10 may further comprise a transverse link 62 having left 64 and right ends 64', each end having an aperture for mounting the link 62 on each respective upper pedicular screw 18, 18'. Because each end 64, 64' is mounted between each upper nut and each upper connector, in use, the link member 62 prevents pivotable movement of each upper nut.

It is understood that the prosthesis 10 may be pre-assembled in such a way that the upper lateral projection 42 (or 42') of the member 20 (or 20') is pre-assembled with the upper connector 14 (or 14'), and the lower connector 12 (or 12') is pre-assembled with the member 20 (or 20'). Any such pre-assembly, may be made so as to facilitate the assembly of the prosthesis 10 by a person skilled in the art, e.g. a medical surgeon, on the spinal segment to be instrumented.

Indeed, the surgeon performs the anchoring of the pedicular screws 16, 16', and 18, 18' in each pedicle ($V_P$) of the vertebrae ($V_L$, $V_U$) of the spinal segment to be instrumented followed by assembly, on each screw, of the respective lower connector 12 (or 12') and the respective upper connector 14 (or 14'). The surgeon may then assemble each lower connector 12 (or 12') and upper connector 14 (or 14') between them by using the member 20 (or 20'). In order to do this, the surgeon may carry out a distance and/or angular adjustment of the member 20 (or 20'), which may require pivotable movement of the member 20 (or 20') relative to the lower axis 22 (or 22'), pivotable movement of the upper connector 14 (or 14') relative to the upper axis 24 (or 24'), pivotable movement of the member 20 (or 20') relative to the first lower pivoting axis 48 (or 48'), pivotable movement of the member 20 (or 20') relative to the second lower pivoting axis 53 (or 53'), and/or pivotable movement of the member 20 (or 20') via the ball 52 within the socket 54. The person skilled in the art will appreciate that the length of the member 20 (or 20') may vary thus allowing adjustment for each individual patient and/or for each vertebra.

Once such adjustment(s) is (are) made, or alternatively while making such adjustment(s), the person skilled in the art will appreciate that the lower connector 12 (or 12') and the upper connector 14 (or 14') are coupled on their respective pedicular screw 16 (or 16') and 18 (or 18') by fastening means, which can be adjusted for each individual patient or each individual pedicular screw, as judged by the surgeon and/or quantified to a desired tightening torque. It is to be understood that once installed and when the nuts 60, 60', 61, 61' are tightened, the upper connectors 14, 14' remain in place and each ball 52 is maintained in place in each socket 54 such that movement of the ball 52 relative to the socket 54 is prevented and each lower connector 12 (or 12') can pivot with respect to the sleeve 46 relative to the axes 22 (or 22'), 48 (or 48') and/or 53 (or 53').

Figure 7:
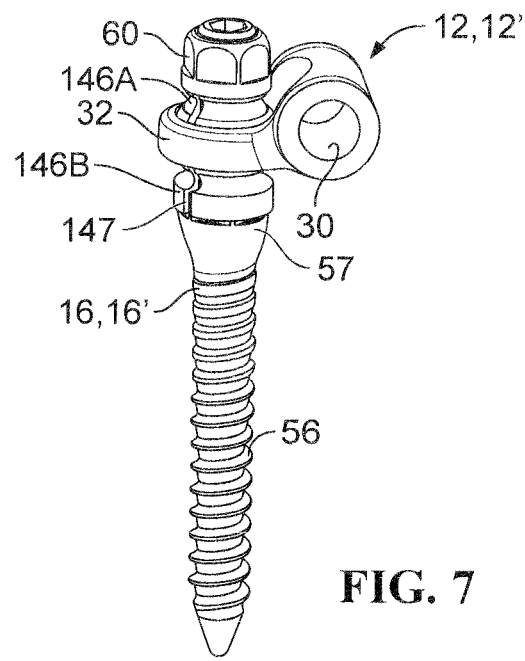
FIG. 7 is an enlarged perspective view of one pedicular screw, lower connector, sleeve and nut, the sleeve being constructed in accordance with another embodiment.
Figure 8:
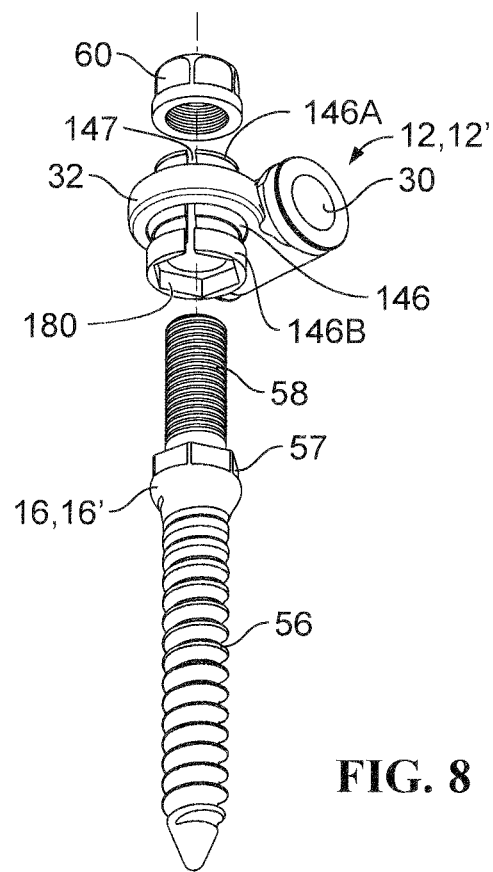
FIG. 8 is an enlarged exploded perspective view of the pedicular screw, lower connector, sleeve and nut shown in FIG. 7.

FIGS. 7 and 8 show another embodiment of a sleeve 146 having an upper portion 146A and a bottom portion 146B, the height of the sleeve 146 being larger than the one of the connecting portion 32 such the respective top and bottom portions 146A, 146B extend above and below the connecting portion 32 of the lower connector 12 (or 12'). As best shown in FIG. 8, the bottom portion 146B extends well below the connecting portion 32 and may have an inner wall 180 that defines an inner hexagonal shape complementary to the shape of the shoulder 57. Once the sleeve 146 is installed within the second aperture 34 of the lower connector 12 (or 12'), the bottom portion 146B at least partially covers the shoulder 57 for preventing any pivotable movement of the sleeve 146 and the upper portion 146A is above the connecting portion 32, thereby allowing each lower nut 60 (or 60') to abut each sleeve 146, and once tightened, maintaining in place each sleeve 146 on each lower pedicular screw 16 (or 16'). Because the nut 60 (or 60') does not contact the connection portion 32 of the lower connector 12 (or 12'), pivotable movements of the lower connector 12 (or 12') with respect to the sleeve 46 is therefore permitted.

Figure 9:
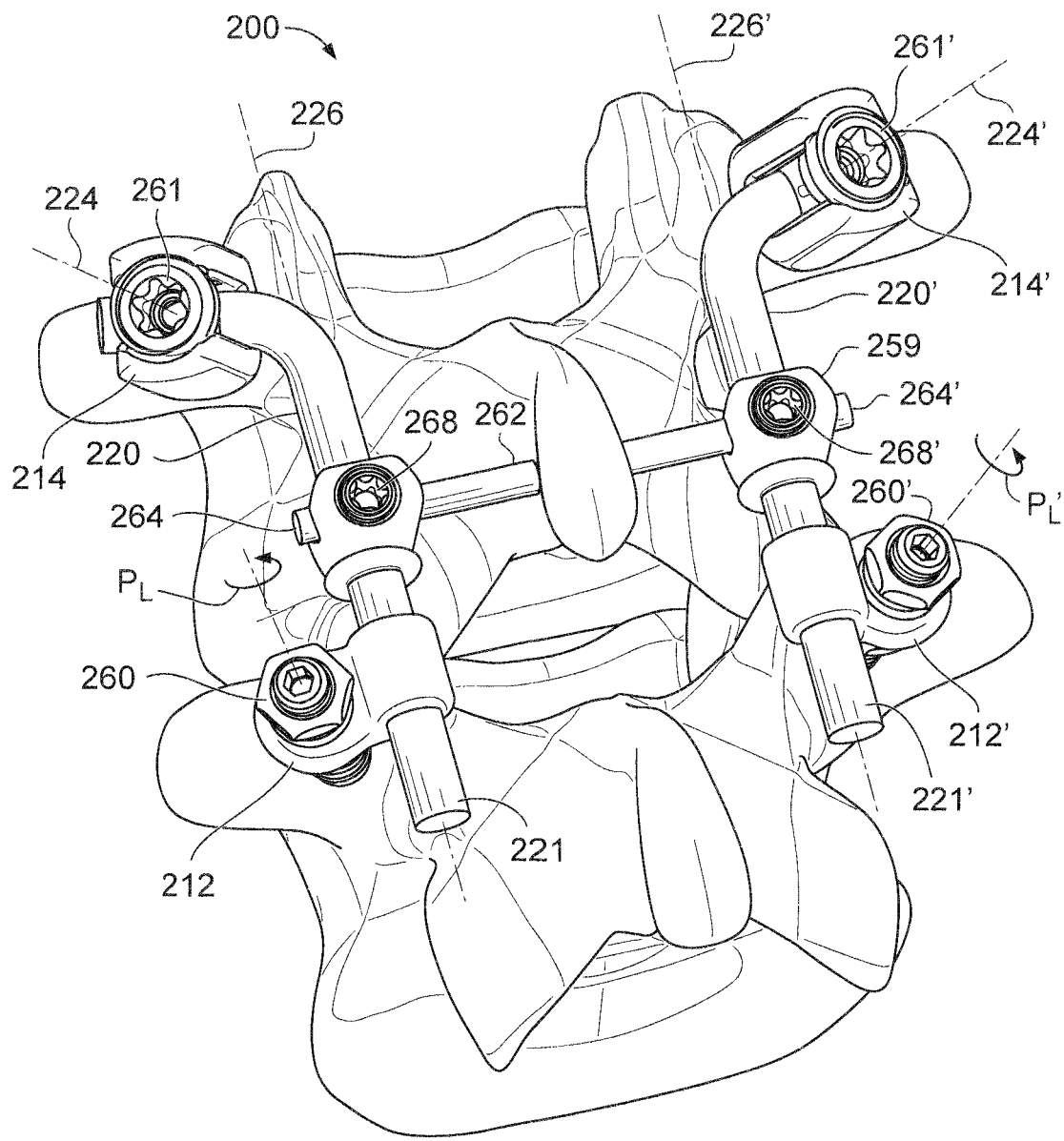
FIG. 9 is a perspective view of a posterior lumbar joint prosthesis in accordance with another embodiment of the present invention.

In FIG. 9, an instrumented spinal segment of a vertebral column is shown of which an upper and lower lumbar vertebrae $V_U$, $V_L$ are connected to each other on each side of the lumbar column by a posterior lumbar joint prosthesis 200 constructed in accordance with another embodiment of the present invention.

Figure 10:
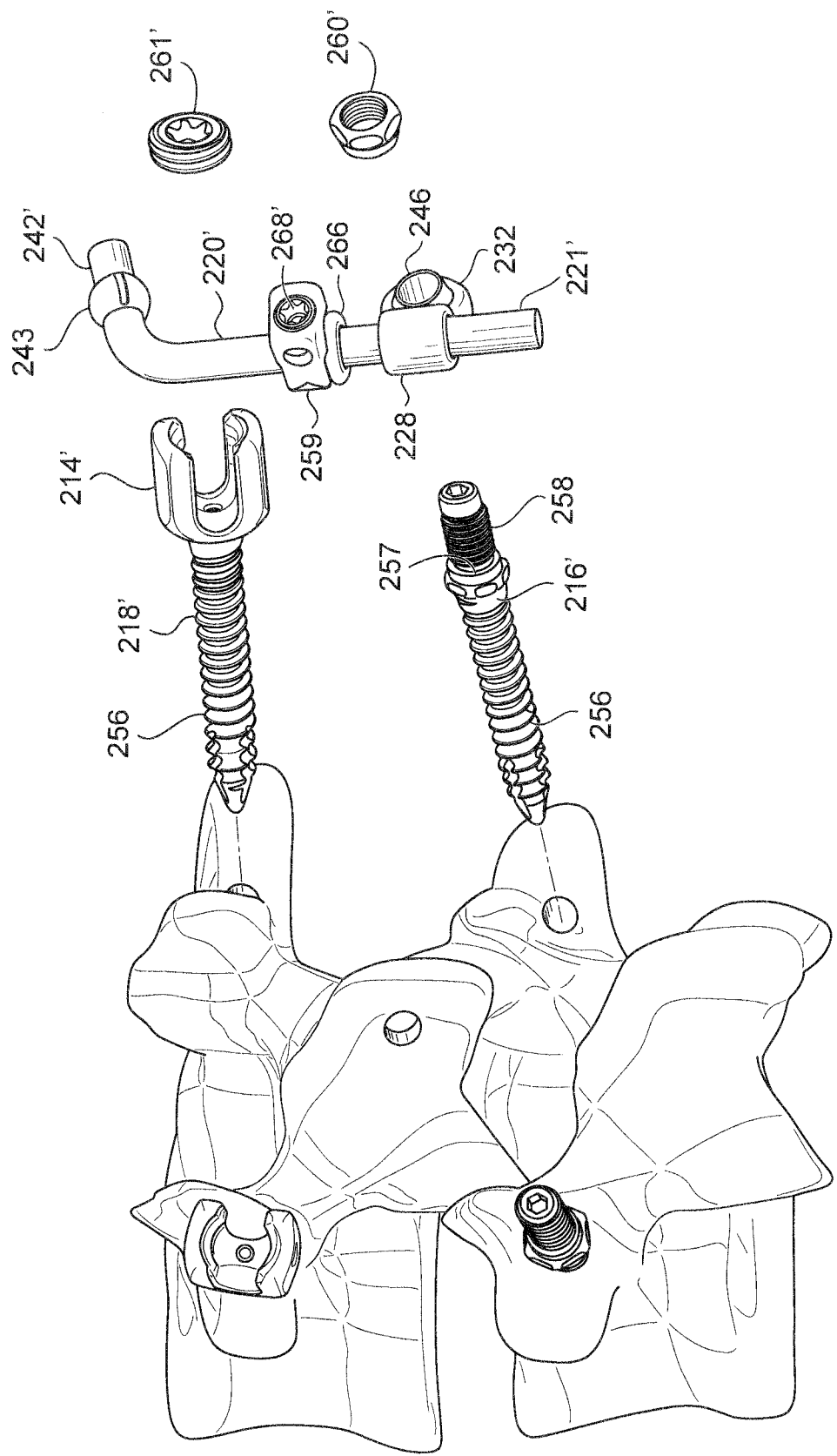
FIG. 10 is a perspective view showing two pedicular screws anchored in the left upper and lower lumbar vertebrae ($V_U$, $V_L$) of the instrumented spinal segment, two pedicular screws to be anchored in the right upper and lower lumbar vertebrae ($V_U$, $V_L$) and right upper and lower connectors with a right member linking them, of the prosthesis shown in FIG. 9.
Figure 11:
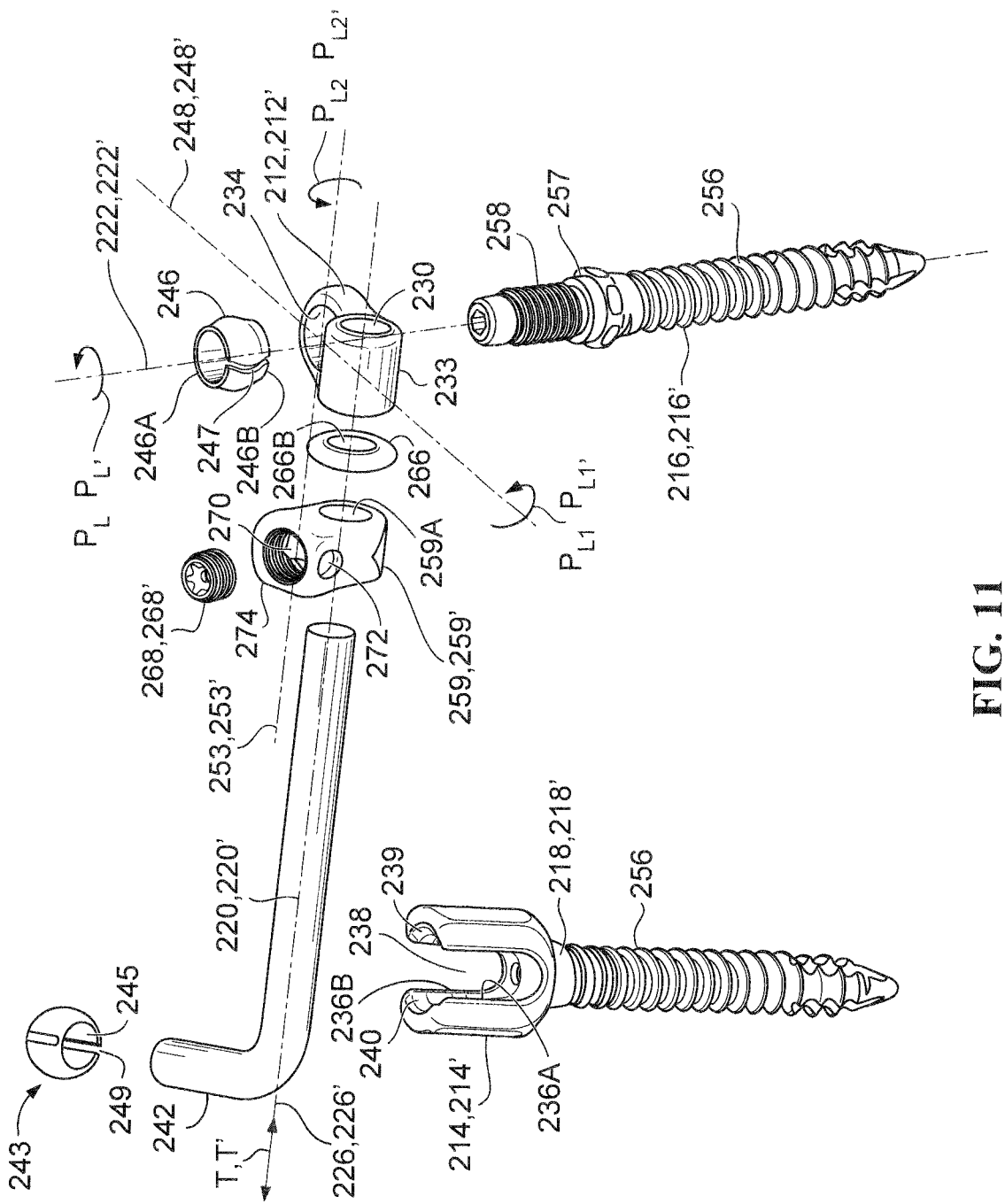
FIG. 11 is an enlarged exploded perspective view of the right upper and lower connectors and the right member shown in FIG. 9.

Referring to FIGS. 9 to 11, the prosthesis 200 has left and right lower connectors 212, 212', which are coupled to respective left and right lower pedicular screws 216, 216', as well as left and right upper connecting portions 214, 214' provided on respective left and right upper pedicular screws 218, 218'. The screws 216, 216' are anchored in the left and right pediculi $V_P$ of the lower lumbar vertebra $V_L$ and the screws 218, 218' are anchored in the left and right pediculi $V_P$ of the upper vertebra $V_U$.

Referring to FIGS. 10 and 11, the lower pedicular screw 216 (or 216') has an upper threaded portion 258, a shoulder 257 and a lower threaded portion 256 that is adapted to be anchored in the pedicle $V_P$. The upper pedicular screw 218 (or 218') has a threaded portion 256 that is similarly adapted to be anchored in the pedicle $V_P$.

In one embodiment, the pedicular screws 216, 216' and/or 218, 218' may be cannulated with side openings. Such openings may allow the injection, for instance, of biological cement intended to improve anchoring within each lower and upper lumbar vertebrae $V_L$, $V_U$ of the spinal segment to be instrumented.

The person skilled in the art will appreciate that the threaded portion 256 of each pedicular screw is intended for anchoring the pedicular screw within the bony body of the pedicles $V_P$ of each respective lower and upper lumbar vertebrae $V_L$, $V_U$ of the spinal segment to be instrumented according to methods that are known in the art.

As best shown in FIGS. 9 and 11, the lower pedicular screw 216' (or 216) defines a right (or left) lower axis 22' (or 22). The prosthesis 200 comprises a left member 220 for linking the left lower connector 212 and the upper connecting portion 214 on the left side of the lumbar vertebrae $V_L$, $V_U$ and a right member 220' for linking the right lower connector 212' and the upper connecting portion 214' on the right side of the lumbar vertebrae $V_L$, $V_U$. The left and right members 220, 220' extend along respective left and right member axes 226, 226'.

As best shown in FIGS. 9 to 11, each of the left and right lower connectors 212, 212' has a body 228 having an internal peripheral wall defining a first aperture 230 encircling the member axis 226 (or 226'), and a connecting portion 232 having a second aperture 234 encircling the lower axis 222 (or 222'). The member 220 (or 220') extends through the first aperture 230 of the lower connector 212 (or 212') and the lower pedicular screw 216 (or 216') extends through the second aperture 234. As shown in FIG. 11, the lower axis 222 (or 222') is a "vertical" axis while the member axis 226 (or 226') is a "horizontal" axis, the lower axis 222 (or 222') being spaced from the member axis 226 (or 226').

As best shown in FIGS. 10 and 11, the connecting portion 232 of the lower connector 212 (or 212') has an internal concave peripheral surface and the prosthesis 200 has a sleeve 246 that is at least partially received within the second aperture 234 of the connecting portion 232, the sleeve 246 having a spherical portion having an external convex surface that is complementary to the internal concave peripheral surface while there is a minimum clearance between these surfaces such that the lower connector 12 (or 12') can pivot relative to the sleeve 246. As shown in FIG. 11, the sleeve 246 may have an upper portion 246A extending above the spherical portion and a bottom portion 246B extending below the spherical portion of the sleeve 246. The sleeve 246 has a split 247 for allowing its insertion inside the second aperture 234 of the connecting portion 232 of the lower connector 212 (or 212') before installing the lower connector 212 (or 212') on the lower pedicular screw 216 (or 216').

Because the lower connector 212 (or 212') is pivotably mounted on the sleeve 246, during use, movement of one of the upper vertebra pedicle relative to the other upper vertebra pedicle imparts pivotable movement $P_L$ (or $P_L'$) of the member 220 (or 220') relative to the lower axis 222 (or 222') and/or imparts translational movement T (or T') of the member 220 (or 220') along the member axis 226 (or 226').

Referring to FIGS. 10 and 11, because the sleeve 246 is mounted and retained in place on the lower pedicular screw 216 (or 216'), and because the lower connector 212 (or 212') is pivotably mounted on the sleeve 246, pivotable movement $P_{L1}$ (or $P_{L1}'$) of the member 220 (or 220') relative to a first lower pivoting axis 248 (or 248') intersecting the member axis 226 (or 226') and the lower axis 222 (or 222') is permitted. It is understood that when the member 220 (or 220') incurs a pivotable movement $P_{L1}$ (or $P_{L1}'$) relative to the first lower pivoting axis 248 (or 248'), so does the lower connector 212 (or 212') with respect to the sleeve 246. Indeed, pivotable movement $P_{L1}$ (or $P_{L1}'$) of the member 220 (or 220') relative to the lower pivoting axis 248 (or 248') imparts similar movement $P_{L1}$ (or $P_{L1}'$) of the body 228 that, in turn, imparts similar movement to the connecting portion 232, and thus to the whole lower connector 212 (or 212') with respect to the sleeve 246, which remains in place on the lower pedicular screw 216 (or 216').

With continuing reference to FIG. 11, there is also a second lower pivoting axis 253 (or 253'), parallel to the member axis 226 (or 226') and that intersects the first lower pivoting axis 248 (or 248') and the lower axis 222 (or 222'). Because the lower connector 212 (or 212') is pivotably mounted on the sleeve 246, pivotable movement $P_{L2}$ (or $P_{L2}'$) of the member 220 (or 220') relative to the second lower pivoting axis 253 (or 253') is also permitted. Again, it is understood that when the member 220 (or 220') incurs a pivotable movement $P_{L2}$ (or $P_{L2}'$) relative to the second lower pivoting axis 253 (or 253'), so does the lower connector 212 (or 212') with respect to the sleeve 246, which remains in place on the lower pedicular screw 216 (or 216').

As shown in FIG. 1, the first lower pivoting axis 248 (or 248') is a "horizontal" axis intersecting the lower axis 222 (or 222') at an angle of 90°. Similarly, the second lower pivoting axis 253 (or 253') is a "horizontal" axis intersecting the lower axis 222 (or 222') at an angle of 90°.

Upon lateral flexion of one of the upper and lower vertebrae relative to the other, each lower connector 212 (or 212') is therefore capable of pivotable movements relative to the sleeve 246 such that each member can pivot relative to the first lower pivoting axis (pivotable movement $P_{L1}$, $P_{L1}'$) and the second pivoting axis (pivotable movement $P_{L2}$, $P_{L2}'$). The range of pivotable movement of the member 220 (or 220') relative of the first lower pivoting axis 248 (or 248') can vary from −12° to 12° and the range of pivotable movement of the member 220 (or 220') relative of the second lower pivoting axis 253 (or 253') can vary from −12° to 12°.

Again, it is understood that pivotable movements $P_{L1}$ (or $P_{L1}'$), $P_{L1}$ (or $P_{L1}'$) and/or $P_{L2}$ (or $P_{L2}'$) of the member 220 (or 220') imparts corresponding pivotable movements of the lower connector 212 (or 212') with respect to the sleeve 246.

The prosthesis 200 allows flexing and extension movements side flexing, and rotation concomitant with side flexing of the upper and lower lumbar vertebrae $V_U$, $V_L$ of the instrumented spinal segment.

Referring to FIGS. 10 and 11, each of the left and right members 220, 220' has a lower end 221 and an upper lateral projection 242 that is partly received within an aperture defined by an inner wall 245 of a ball ring 243 having a split 249. It is understood that the lower end 221 may have a stop or means such that, during use, movement T (or T') of the member 220 (or 220') along the member axis towards the upper vertebra $V_U$ is prevented.

The prosthesis 200 also comprises two mid-elements 259 and two absorbing rings 266, each mid-element 259 having a body defining a first aperture 259A encircling the member axis 226 (or 226') and each absorbing ring 266 having a body defining an aperture 266A encircling the member axis 226 (or 226'). Each mid-element 259 and each absorbing ring 266 are mounted on the member 220 (or 220'). The absorbing ring 266 is made of a suitable material to reduce shock impacts that can be transmitted to the lower pedicular screw 216 (or 216').

As best shown in FIGS. 10 and 11, each of the left and right upper connecting portions 214, 214' has a body having lateral apertures 236A, 236B, an upper aperture 239 encircling the upper axis 224 (or 224') and an internal peripheral wall 240 defining a cavity 238. The cavity 238 receives the upper lateral projection 242 of the member 220 (or 220'). The upper portion of the peripheral wall 240 has a threaded portion. The ball ring 243 has an external convex surface that is complementary to the internal peripheral wall 240 while there is a minimum clearance between this external convex surface and the internal peripheral wall 240 such that the upper lateral projection 242 of the member 220 (or 220') can pivot relative to the sleeve 243 during installation of each member.

As shown in FIGS. 9 and 10, a tightening nut 260 (or 260') is used to affix the lower connector 212 (or 212') on the lower pedicular screw 216 (or 216'). The tightening nut 260 is fastened on the threaded portion 258 of each lower pedicular screw, according to general techniques that are well known in the art, and rests on top of the sleeve 246 in order to prevent any pivotable movement of the sleeve 246 and maintaining in place the sleeve 246 on the lower pedicular screw 216 (or 216').

Also as shown in FIGS. 9 and 10, an upper nut 261 (or 261') is screwed in the threaded portion of the inner wall 240 of each upper connecting portion 214 (or 214') on the upper pedicular screw 218 (or 218'). Using techniques well known in the art, each upper nut 261 (or 261') is tightened such that each upper nut 261 (or 261') applies pressure on the ball ring 243, which, because of the split 249, is slightly deformable such that the upper lateral projection 242 is maintained in place in the upper connecting portion 214 (or 214') for preventing any movement of the upper lateral projection 242.

As shown in FIGS. 9 to 11, the mid-element 259 (or 259') may further include a second aperture 272 and the prosthesis 200 may include a transverse link member 262 having left and right ends 264, 264', each end being partly mounted within the aperture 272 on the respective mid-element 259, 259', such that during use, the left and right ends 264, 264' rest on a portion of the upper surface of the respective member 220, 220'. The mid-element 259 (or 259') may further include a third aperture 270 having an inner threaded wall 274 for receiving a tightening nut 268 (or 268'). Using techniques well known in the art, each tightening nut 268, 268' is tightened such that each tightening nut 268, 268' applies pressure on the respective left and right ends 264, 264' such that the mid-elements 259 and the transverse link member 262 are maintained with respect to the members 220, 220'. As seen in FIG. 9, the link member 262 passes through the bony body of the upper vertebra. In use, because the link member 262 maintains a constant distance between the members 220, 220', it prevents transfer of pivotable forces to the upper pedicular screws 218, 218'.

The person skilled in the art will appreciate that the installation method for the prosthesis 200 may be performed substantially as described for the prosthesis 10 in respect of similar elements, including the distance and/or angular adjustment of the member 220 (or 220') similar to those described for the member 20 (or 20').

The prosthesis 10 (or 200) allows the above described movement of the upper and lower lumbar vertebrae due to the prosthesis structure and design, which are adapted to: the spacing between the pedicles $V_P$ of the upper and lower lumbar vertebrae $V_U$, $V_L$ of the spinal segment to be instrumented, the spacing between the pedicular screws, and the differences in the angle and the depth of the pedicular screws anchored in the lumbar vertebrae $V_U$, $V_L$.

The person skilled in the art will appreciate that the prosthesis 10 (or 200) may be made of any surgically acceptable materials. In one embodiment, the materials comprise, but are not limited to, chrome-cobalt and TA6V titanium alloy. The materials may also comprise ceramic, polyethylene and other suitable materials used in prostheses known in the art.

The person skilled in the art will also appreciate that the prosthesis 10 (or 200) may also comprise, optionally flexible, protective elements having a shape which is complementary to the external portion of any or all elements of the prosthesis 10 (or 200) in order to envelope these elements so as to protect it these from external human tissues and/or vice-versa.

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. A posterior lumbar joint prosthesis intended for an upper and a lower lumbar vertebrae, the upper lumbar vertebra having left and right upper pedicles and the lower lumbar vertebra having left and right lower pedicles, said prosthesis comprising:
 (a) a left upper pedicular screw extending along a left upper axis, said left upper pedicular screw having a lower threaded portion configured to be anchored in the left upper pedicle;
 (b) a right upper pedicular screw extending along a right upper axis, said right upper pedicular screw having a lower threaded portion configured to be anchored in the right upper pedicle;
 (c) a left lower pedicular screw extending along a left lower axis, said left lower pedicular screw having upper and lower threaded portions, said lower threaded portion configured to be anchored in the left lower pedicle;
 (d) a right lower pedicular screw extending along a right lower axis, said right lower pedicular screw having upper and lower threaded portions, said lower threaded portion configured to be anchored in the right lower pedicle;
 (e) left and right lower connectors, each respectively coupled to said left and right lower pedicular screws;
 (f) a left member for linking said left upper pedicular screw and said left lower connector, said left member extending along a left member axis and having a lower end and an upper lateral projection linked to said left upper pedicular screw, said left member axis being spaced from said left lower axis;
 (g) a right member for linking said right upper pedicular screw and said right lower connector, said right member extending along a right member axis and having a lower end and an upper lateral projection linked to said right upper pedicular screw, said right member axis being spaced from said right lower axis;
 (h) a U-shaped right upper connecting portion provided at an end of said right upper pedicular screw;
 (i) a U-shaped left upper connecting portion provided at an end of said left upper pedicular screw;
 (j) a right ball ring of the right member, the right ball ring fitting in the U-shape of the right upper connecting portion; and
 (k) a left ball ring of the left member, the left ball ring fitting in the U-shape of the left upper connecting portion,
 wherein each of said left and right lower connectors has a body having an internal peripheral wall defining a first aperture encircling each member axis and a connecting portion having a second aperture encircling each lower axis, wherein each lower pedicular screw extends through said second aperture of each lower connector and wherein each member extends through said first aperture of each lower connector;
 wherein said prosthesis comprises left and right sleeves, each of said left and right sleeves having a spherical portion with an external convex peripheral surface and being mounted on said upper threaded portion of each lower pedicular screw and within said second aperture of said connecting portion of each lower connector and
 wherein said connecting portion of each lower connector has an internal concave peripheral wall following said external convex peripheral surface of said sleeve such that each lower connector is pivotably mounted with respect to said sleeve and such that, in use, lateral flexion of one of the upper and lower vertebrae relative to the other imparts either or both (i) movement of one member along said member axis with respect to said first aperture of said lower connector and (ii) pivotable movement of said member relative to said lower axis, and further imparts pivotable movement of said member relative to either or both (iii) a first lower pivoting axis intersecting said member axis and said lower axis and (iv) a second lower pivoting axis, parallel to said member axis, and intersecting said lower axis and said first lower pivoting axis; and wherein said prosthesis comprises left and right lower nuts, wherein each sleeve has an upper portion extending above said connecting portion of said lower connector and wherein each lower nut is tightened on said upper threaded portion of each lower pedicular screw such that it abuts and maintains in place each sleeve while allowing pivotable movements of said lower connector with respect to said sleeve.

2. A posterior lumbar joint prosthesis intended for an upper and a lower lumbar vertebrae, the upper lumbar vertebra having left and right upper pedicles and the lower lumbar vertebra having left and right lower pedicles, said prosthesis comprising:
- (a) a left upper pedicular screw extending along a left upper axis, said left upper pedicular screw having a lower threaded portion configured to be anchored in the left upper pedicle;
- (b) a right upper pedicular screw extending along a right upper axis, said right upper pedicular screw having a lower threaded portion configured to be anchored in the right upper pedicle;
- (c) a left lower pedicular screw extending along a left lower axis, said left lower pedicular screw having upper and lower threaded portions, said lower threaded portion configured to be anchored in the left lower pedicle;
- (d) a right lower pedicular screw extending along a right lower axis, said right lower pedicular screw having upper and lower threaded portions, said lower threaded portion configured to be anchored in the right lower pedicle;
- (e) left and right lower connectors, each respectively coupled to said left and right lower pedicular screws;
- (f) a left member for linking said left upper pedicular screw and said left lower connector, said left member extending along a left member axis and having a lower end and an upper lateral projection linked to said left upper pedicular screw, said left member axis being spaced from said left lower axis;
- (g) a right member for linking said right upper pedicular screw and said right lower connector, said right member extending along a right member axis and having a lower end and an upper lateral projection linked to said right upper pedicular screw, said right member axis being spaced from said right lower axis;
- (h) a U-shaped right upper connecting portion provided at an end of said right upper pedicular screw;
- (i) a U-shaped left upper connecting portion provided at an end of said left upper pedicular screw;
- (j) a right ball ring of the right member, the right ball ring fitting in the U-shape of the right upper connecting portion; and
- (k) a left ball ring of the left member, the left ball ring fitting in the U-shape of the left upper connecting portion, wherein each of said left and right lower connectors has a body having an internal peripheral wall defining a first aperture encircling each member axis and a connecting portion having a second aperture encircling each lower axis, wherein each lower pedicular screw extends through said second aperture of each lower connector and wherein each member extends through said first aperture of each lower connector;

and wherein, in use, lateral flexion of one of the upper and lower vertebrae relative to the other imparts either or both (i) movement of one member along said member axis with respect to said first aperture of said lower connector and (ii) pivotable movement of said member relative to said lower axis.

3. A posterior lumbar joint prosthesis intended for an upper and a lower lumbar vertebrae, the upper lumbar vertebra having left and right upper pedicles and the lower lumbar vertebra having left and right lower pedicles, said prosthesis comprising:
- (a) a left upper pedicular screw extending along a left upper axis, said left upper pedicular screw having a lower threaded portion configured to be anchored in the left upper pedicle;
- (b) a right upper pedicular screw extending along a right upper axis, said right upper pedicular screw having a lower threaded portion configured to be anchored in the right upper pedicle;
- (c) a left lower pedicular screw extending along a left lower axis, said left lower pedicular screw having upper and lower threaded portions, said lower threaded portion configured to be anchored in the left lower pedicle;
- (d) a right lower pedicular screw extending along a right lower axis, said right lower pedicular screw having upper and lower threaded portions, said lower threaded portion configured to be anchored in the right lower pedicle;
- (e) left and right lower connectors, each respectively coupled to said left and right lower pedicular screws;
- (f) a left member for linking said left upper pedicular screw and said left lower connector, said left member extending along a left member axis and having a lower end and an upper lateral projection linked to said left upper pedicular screw, said left member axis being spaced from said left lower axis;
- (g) a right member for linking said right upper pedicular screw and said right lower connector, said right member extending along a right member axis and having a lower end and an upper lateral projection linked to said right upper pedicular screw, said right member axis being spaced from said right lower axis;
- (h) a U-shaped right upper connecting portion provided at an end of said right upper pedicular screw;
- (i) a U-shaped left upper connecting portion provided at an end of said left upper pedicular screw;
- (j) a right ball ring of the right member, the right ball ring fitting in the U-shape of the right upper connecting portion; and
- (k) a left ball ring of the left member, the left ball ring fitting in the U-shape of the left upper connecting portion, wherein each of said left and right lower connectors has a body having an internal peripheral wall defining a first aperture encircling each member axis and a connecting portion having a second aperture encircling each lower axis, wherein each lower pedicular screw extends through said second aperture of each lower connector and wherein each member extends through said first aperture of each lower connector; and wherein said prosthesis comprises left and right sleeves, each of said left and right sleeves having a spherical portion with an external convex peripheral surface and being mounted on said upper threaded portion of each lower pedicular screw and within said second aperture of said connecting portion of each lower connector and wherein said connecting portion of each lower connector has an internal concave peripheral wall following said external convex peripheral surface of said sleeve such that each lower connector is pivotably mounted with respect to said sleeve and such that, in use, lateral flexion of one of the upper and lower vertebrae relative to the other imparts either or both (i) movement of one member along said member axis with respect to said first aperture of said lower connector and (ii) pivotable movement of said member relative to said lower axis, and further imparts pivotable movement of said member relative to either or both (iii) a first lower pivoting axis intersecting said member axis and said lower axis and (iv) a second lower pivoting axis, parallel to said member axis, and intersecting said lower axis and said first lower pivoting axis.

* * * * *